(12) United States Patent
Chiou et al.

(10) Patent No.: US 8,710,297 B2
(45) Date of Patent: Apr. 29, 2014

(54) GLYCOSYLTRANSFERASE PROMOTER

(75) Inventors: Shu-Jiau Chiou, Hsinchu (TW);
Cheng-Yu Lee, Hsinchu (TW);
Pei-Hsuan Wei, Yunlin County (TW);
Jui-Hung Yen, New Taipei (TW);
Cheng-Li Fang, Hsinchu County (TW)

(73) Assignee: Industrial Technology Research Institute, Hsinchu (TW)

( * ) Notice: Subject to any disclaimer, the term of this patent is extended or adjusted under 35 U.S.C. 154(b) by 242 days.

(21) Appl. No.: 13/187,931

(22) Filed: Jul. 21, 2011

(65) Prior Publication Data

US 2012/0185975 A1 Jul. 19, 2012

(30) Foreign Application Priority Data

Jan. 19, 2011 (TW) .............................. 100101942 A

(51) Int. Cl.
*C12N 15/82* (2006.01)
*C07H 21/04* (2006.01)
*C12N 15/05* (2006.01)
*C12N 15/00* (2006.01)

(52) U.S. Cl.
USPC ....... 800/287; 536/24.1; 435/419; 435/320.1; 435/468; 800/278

(58) Field of Classification Search
None
See application file for complete search history.

(56) References Cited

U.S. PATENT DOCUMENTS

| 5,459,252 | A | 10/1995 | Conkling et al. |
| 5,837,848 | A | 11/1998 | Ely et al. |
| 5,837,876 | A | 11/1998 | Conkling et al. |
| 6,518,483 | B1 | 2/2003 | Bruce et al. |
| 7,674,893 | B2 | 3/2010 | Milligan et al. |
| 2005/0257286 | A1* | 11/2005 | Vijaybhaskar et al. ....... 800/279 |

OTHER PUBLICATIONS

Chiou et al_Planta_232_963_2010.*
Potenza_In Vitro Cell Dev Biol Plant_40_1_2004.*
Vaughan et al., J Exp Biol 57(14)3901-10 (2006).*
Donald & Cashmore, EMBO J 9:1717-26 (1990).*
Kim et al., Plant Mol Biol 24:105-17 (1994).*
Dolferus et al., Plant Physiol 105:1075-87 (1994).*
Hirotani_Planta_210_1006_2000.*
Cai et al., (Life Sci 74:2157-84 (2004).*
Subramanian et al., "The promoters of two is0flavone synthase genes respond differentially to nodulation and defense signals in transgenic soybean roots," Plant Molecular Biology, 2004, pp. 623-639, vol. 54.

(Continued)

*Primary Examiner* — Medina A Ibrahim
*Assistant Examiner* — Russell Boggs
(74) *Attorney, Agent, or Firm* — Muncy, Geissler, Olds & Lowe, P.C.

(57) ABSTRACT

A glycosyltransferase promoter and a recombinant nucleic acid, plant cell and transgenic plant containing thereof are provided. The promoter includes a nucleotide sequence as set forth in any one of SEQ ID NOs: 1~7, a fragment having at least 10 contiguous bases of any one of SEQ ID NOs: 1~7 or a combination thereof, or a nucleotide sequence having 90% or more identity to the nucleotide sequence as set forth in any one of SEQ ID NOs: 1~7.

28 Claims, 8 Drawing Sheets

```
                                                       AAGCTTCTAGAACGCGTAGGGGTAT...-826
TAGAGGAAGTCAAAGTTCGAGGAAACTATTAAACGCTTGAAACGTCTCTCATGCCAGTTGAACACTTGTACTTCA...-751
AGAAGAATACAGATTGGGAAAAAGATTATCAAATTGAACTTCTTTTCATGACTTGTTTGCTCACATAATTCCAC...-676
ATTTCTGATGAATTAAGAAAGACTAATGAAAATTTAATTCTGTAAAATTAATTTCTTATTTTATTTTTTCGATT...-601
TTGTAGATGTTATTTATATTTGGTAAACTAATTTTATTATAAACTCAAGTAACCGTTAATTGTGAGCTTGTCGTT...-526
CCTACAAGAGTTTAAGCCTTCTAAACTCATTAACTGCATTTATGGATACTATCCATATATAAGAGAAAATCTATT...-451
AAATTCTGATTTCTTTCCAAATATAGTTTAATGTCAAATACATTAATCATCATAGACACACCCTATTTTAATATA...-376
AATACAAACGTCAAATATTAAATTTTTACAAAAAAAAATATAGCAATTCAATTTCAAGATAAAGAAAAATATCAA...-301
AAACTCAATATTCACAAATAAAAGTATAATAACTCGATCATAAACTAAACTGCACACAATCCAACTTTTTTTTT...-226
AAGAGTATCCTGTATGAATGTAGGAATTAAATTACATGATAATTGACTCAATTTGACTCTTCCAAGTATCCAATT...-151
GGTTTCTTCTATATGGTCGACACGTGTCCAATTCCGATAGACTCTAATCTAGAAGACCAGATAAACGATACGTAA...-76
GCAAGTACGTCATCAAATAAGCTTCTCCTCTCTCTGTTTCTATAATTATATATTAGTCGAGACTTCATTGAGCAA...-1
+1
AATCCTATATTGCATCCTTTCTCATGCAGGCCACCATAAATATTCCATTCCAAGAATTCCAAATTTGCAAATATA...+75
CACATAATTAAGATCTTTCCATTTTACAGTGTTGAA............................................+111
```

(56) References Cited

OTHER PUBLICATIONS

Fehlberg et al., "The promoter of the leghaemoglobin gene VfLb29: functional analysis and identification of modules necessary for its activation in the infected cells of root nodules and in the arbuscule-containing cells of mycorrhizal roots," Journal of Experimental Biology, Mar. 2005, pp. 799-806, vol. 56, No. 413.

Jones et al., "The promoter from SIREO, a highly-expressed, root-specific *Solanum lucopersicum* gene, directs expression to cortex of mature roots," Functional Plant Biology, 2008, pp. 1224-1233, vol. 35, No. 12.

Jeong et al., "Root-specific expression of OsNAC10 inproves drought tolerance and grain yield in rice under field drought conditions," Plant Physiology, May 2010, pp. 185-197, vol. 153.

Liu et al., "Root-specific expression of a western white pine PR10 gene is mediated by different promoter regions in transgenic tobacco," Plant Molecular Biolology, 2003, pp. 103-120, vol. 52.

Liu et al., "Molecular cloning of a pathogen/wound-inducible PR10 promoter form *Pinus monticola* and characterization in transgneic *Arabidopsis* plants," Planta, 2005, pp. 159-169, vol. 221.

Du et al., "Isolation and functional characterization of a waterlogging-induced promoter from maize," Plant Cell Rep, 2010, pp. 1269-1275, vol. 29.

Xiao et al., "Isolation and characterization of root-specific phosphate transporter promoters from *Medicago truncatula*," Plant Biol., 2006, pp. 439-449, vol. 8.

Vijaybhaskar et al., "Identification of a root-specific glycosyltransferase from *Arabidopsis* and characterization of its promoter," J. Biosci., Jun. 2008, pp. 185-193, vol. 33, No. 2.

Rouster et al., "Identification of a methyl jasmonate-responsive region in the promoter of a lipoxygenase 1 gene expressed in barley grain," The Plant Journal, 1997, pp. 513-523, vol. 11, No. 3.

Vissenberg et al., "Differential expression of AtXTH17, AtXTH18, AtXTH19, and AtXTH20 genes in *Arabidopsis* root. Physiological roles in specification in cell wall contruction," Plant Cell Physiol., 2005, pp. 192-200, vol. 46, No. 1.

Chiou et al., "Chracterization of the *Scutellaria barbata* glycosyltransferase gene and its promoter," Planta, 2010, pp. 963-974, vol. 232.

Vaughan et al., "Chracterization of FaRB7, a near root-specific gene from strawberry (*Fragaria × ananassa* Duch.) and promoter activity analysis in homologous and heterologous hosts," Journal of Experimental Biology, 2006, pp. 3901-3910, vol. 57, No. 14.

Woo et al., "Chracterization of *Arabidopsis* AtUGT85A and AtGUS gene families and their expression in rapidly dividing tissues," Genomics, 2007, pp. 143-153, vol. 90.

Cazzonelli et al., "Characterization of a strong, consitutive mung bean (*Vigna radiata* L.) promoter with a complex mode of regulation in planta," Transgenic Research, 2005, pp. 941-967, vol. 14.

\* cited by examiner

FIG. 1

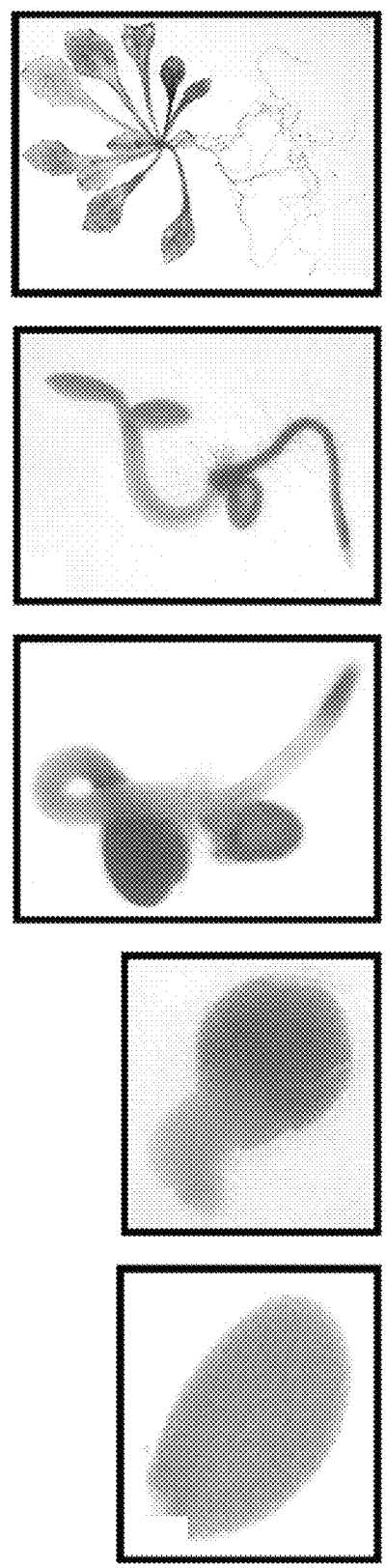

SEQUENCE LISTING

```
<160> NUMBER OF SEQ ID NOS: 24

<210> SEQ ID NO 1
<211> LENGTH: 961
<212> TYPE: DNA
<213> ORGANISM: Scutellaria barbata
<220> FEATURE:

<400> SEQUENCE: 1
aagcttctag aacgcgtagg ggtattagag gaagtcaaag ttcgaggaaa ctattaaacg      60
cttgaaacgt ctctcatgcc agttgaacac ttgtacttca agaagaatac agattgggaa     120
aaaagattat caaattgaac ttcttttcat gacttgtttg ctcacataat tccacatttc     180
tgatgaatta agaaagacta atgaaaattt taattctgta aaattaattt cttattttat     240
tttttcgatt ttgtagatgt tatttatatt tggtaaacta attttattat aaactcaagt     300
aaccgttaat tgtgagcttg tcgttcctac aagagtttaa gccttctaaa ctcattaact     360
gcatttatgg atactatcca tatataagag aaaatctatt aaattctgat ttttttccaa     420
atatagttta atgtcaaata cattaatcat catagacaca ccctatttta atataaatac     480
aacgtcaaat attaaatttt tacaaaaaaa aaatatagca attcaatttc aagataaaga     540
aaaatatcaa aaactcaata ttcacaaata aaagtataat aactcgatca taaactaaac     600
tgcacacaat ccaactttt tttttaagag tatcgtgtat gaatgtagga attaaattac     660
atgataattg actcaatttg actcttccaa gtatccaatt ggtttcttct atatggtcga     720
cacgtgtcca attccgatag actctaatct agaagaccag ataaacgata cgtaagcaag     780
tacgtcatca aataagcttc tcctctctct gtttctataa ttatatatta gtcgagactt     840
cattgagcaa aatcctatat tgcatccttt ctcatgcagg ccaccataaa tattccattc     900
caagaattcc aaatttgcaa atatacacat aattaagatc tttccatttt acagtgttga     960
a                                                                    961

<210> SEQ ID NO 2
<211> LENGTH: 393
<212> TYPE: DNA
<213> ORGANISM: Scutellaria barbata
<220> FEATURE:

<400> SEQUENCE: 2
acaccctatt ttaatataaa tacaacgtca aatattaaat ttttacaaaa aaaaaatata      60
gcaattcaat ttcaagataa agaaaaatat caaaaactca atattcacaa ataaaagtat     120
aataactcga tcataaacta aactgcacac aatccaactt ttttttttaa gagtatcgtg     180
tatgaatgta ggaattaaat tacatgataa ttgactcaat ttgactcttc caagtatcca     240 attggttttct tctatatggt cgacacgtgt ccaattccga tagactctaa tctagaagac     300
cagataaacg atacgtaagc aagtacgtca tcaaataagc ttctcctctc tctgtttcta     360
```

```
taattatata ttagtcgaga cttcattgag caa                            393
```

<210> SEQ ID NO 3
<211> LENGTH: 331
<212> TYPE: DNA
<213> ORGANISM: Scutellaria barbata
<220> FEATURE:

<400> SEQUENCE: 3

```
acaccctatt ttaatataaa tacaacgtca aatattaaat ttttacaaaa aaaaaatata    60
gcaattcaat ttcaagataa agaaaaatat caaaaactca atattcacaa ataaaagtat   120
aataactcga tcataaacta aactgcacac aatccaattt gactcttcca agtatccaat   180
tggtttcttc tatatggtcg acacgtgtcc aattccgata gactctaatc tagaagacca   240
gataaacgat acgtaagcaa gtacgtcatc aaataagctt ctcctctctc tgtttctata   300
attatatatt agtcgagact tcattgagca a                                 331
```

<210> SEQ ID NO 4
<211> LENGTH: 214
<212> TYPE: DNA
<213> ORGANISM: Scutellaria barbata
<220> FEATURE:

<400> SEQUENCE: 4

```
tctagaagac cagataaacg atacgtaagc aagtacgtca tcaaataagc ttctcctctc    60
tctgtttcta taattatata ttagtcgaga cttcattgag caaaatccta tattgcatcc   120
tttctcatgc aggccaccat aaatattcca ttccaagaat tccaaatttg caaatataca   180
cataattaag atctttccat tttacagtgt tgaa                              214
```

<210> SEQ ID NO 5
<211> LENGTH: 44
<212> TYPE: DNA
<213> ORGANISM: Scutellaria barbata
<220> FEATURE:

<400> SEQUENCE: 5

```
tctagaagac cagataaacg atacgtaagc aagtacgtca tcaa                    44
```

<210> SEQ ID NO 6
<211> LENGTH: 111
<212> TYPE: DNA
<213> ORGANISM: Scutellaria barbata
<220> FEATURE:

<400> SEQUENCE: 6

```
aatcctatat tgcatccttt ctcatgcagg ccaccataaa tattccattc caagaattcc    60
aaatttgcaa atatacacat aattaagatc tttccatttt acagtgttga a            111
```

<210> SEQ ID NO 7
<211> LENGTH: 62
<212> TYPE: DNA
<213> ORGANISM: Scutellaria barbata
<220> FEATURE:

<400> SEQUENCE: 7

```
aactttttt tttaagagta tcgtgtatga atgtaggaat taaattacat gataattgac    60
tc                                                                 62
```

<210> SEQ ID NO 8
<211> LENGTH: 28

```
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: primer_bind
<222> LOCATION: (4), (12)
<223> OTHER INFORMATION: n is a, c, g, or t

<400> SEQUENCE: 8
gtgnaatggc tngaagctgg tgacaagc                                             28

<210> SEQ ID NO 9
<211> LENGTH: 28
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: primer_bind
<222> LOCATION: (12), (14)..(15), (23)
<223> OTHER INFORMATION: n is a, c, g, or t

<400> SEQUENCE: 9 ttcttttcc tnanntcatt tanctatc                                              28

<210> SEQ ID NO 10
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 10
attgccagac aacatattga g                                                    21

<210> SEQ ID NO 11
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 11
gtggaagatt cggaatgac                                                       19

<210> SEQ ID NO 12
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 12
gtaatacgac tcactatagg gc                                                   22

<210> SEQ ID NO 13
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 13
tcattggaac aaggataata tgtagct                                              27

<210> SEQ ID NO 14
<211> LENGTH: 19
```

```
<212> TYPE: DNA
<213> ORGANISM: Artificial Sequence
<220> FEATURE:
<223> OTHER INFORMATION: Synthetic oligonucleotide

<400> SEQUENCE: 14
actatagggc acgcgtgga                                              19

<210> SEQ ID NO 15
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 15
tgtaaaatgg aaagatctta attatg                                      26

<210> SEQ ID NO 16
<211> LENGTH: 29
<212> TYPE: DNA
<213> ORGANISM: Artificial Sequence
<220> FEATURE:
<223> OTHER INFORMATION: Synthetic oligonucleotide

<400> SEQUENCE: 16
gtgtccaatt cctgcaggct ctaatctag                                   29

<210> SEQ ID NO 17
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 17
taagagtatc ctgcaggaat gtaggaat                                    28

<210> SEQ ID NO 18
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 18
cataaactaa cctgcaggca atccaac                                     27

<210> SEQ ID NO 19
<211> LENGTH: 31
<212> TYPE: DNA
<213> ORGANISM: Artificial Sequence
<220> FEATURE:
<223> OTHER INFORMATION: Synthetic oligonucleotide

<400> SEQUENCE: 19
tacattaatc ctgcaggaca caccctattt t                                31

<210> SEQ ID NO 20
<211> LENGTH: 32
<212> TYPE: DNA
<213> ORGANISM: Artificial Sequence
<220> FEATURE:
<223> OTHER INFORMATION: Synthetic oligonucleotide

<400> SEQUENCE: 20
tggcctgcat gagaaaggat ccaatatagg at                               32
```

```
<210> SEQ ID NO 21
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 21
ccaacttttt tttcaatttg actc                                              24

<210> SEQ ID NO 22
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 22
gagtcaaatt gaaaaaaaag ttgg                                              24

<210> SEQ ID NO 23
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 23 tcgcccttttt gtctttggcc caatac                                           26

<210> SEQ ID NO 24
<211> LENGTH: 29
<212> TYPE: DNA
<213> ORGANISM: Artificial Sequence
<220> FEATURE:
<223> OTHER INFORMATION: Synthetic oligonucleotide

<400> SEQUENCE: 24
tcacttcctg attattgacc cacactttg                                         29
```

US 8,710,297 B2

GLYCOSYLTRANSFERASE PROMOTER

CROSS REFERENCE TO RELATED APPLICATIONS

This application claims the benefit of Taiwan Patent Application NO. 100,101,942, filed Jan. 19, 2011. The disclosure of the application is incorporated herein by reference.

A sequence listing submitted as a text file via EFS-Web is incorporated herein by reference. The text file containing the sequence listing is named "0965-A23656-US_Seq_Listing.txt"; its date of creation is Jul. 21, 2011; and its size is 7,190 bytes.

BACKGROUND

1. Technical Field

The disclosure relates to an isolated promoter regulating the expression of the gene encoding glycosyltransferase, and in particular relates to a promoter regulating the expression of a foreign gene or reporter gene.

2. Description of the Related Art

Glycosylation is usually the last step in the biosynthesis of many plant secondary metabolites. A conversion to glycosides by plant glycosyltransferases may affect properties of metabolites, such as stability, solubility and bioavailability.

Plant UDP glycosyltransferases (UGTs) belong to the family 1 glycosyltransferase with a highly conserved plant secondary product glucosyltransferase signature. Plant UGTs catalyze the transfer of the glycosyl group from activated nucleotide sugars to secondary metabolites, including flavonoids, anthocyanins, terpenoids, sterols and thiohydroximates [Nagashima et al. (2004) cDNA cloning and expression of isoflavonoid-specific glucosyltransferase from *Glycyrrhiza echinata* cell-suspension cultures. *Planta* 21:456-459]. Several plant flavonoid glycosyltransferases and their substrate preferences have been characterized.

The cauliflower mosaic virus (CaMV) 35S promoter is frequently used for a strong and constitutive gene expression in plant systems. The CaMV 35S promoter, however, may cause sterility, retarded development, altered morphology and transgene silencing. Therefore, it is demanded to develop a novel plant promoter for a high-level or tissue-specific expression of a coding sequence.

SUMMARY

One embodiment of the disclosures provides an isolated promoter which comprises a nucleotide sequence selected from the group consisting of: (a) a nucleotide sequence as set forth in SEQ ID NO:1, (b) a nucleotide sequence containing a deletion at positions 1 to 457 and 851 to 961 of SEQ ID NO:1 as set forth in SEQ ID NO:2, (c) a nucleotide sequence containing a deletion at positions 1 to 457, 613 to 674 and 851 to 961 of SEQ ID NO:1 as set forth in SEQ ID NO:3, (d) a nucleotide sequence containing a deletion at positions 1 to 747 of SEQ ID NO:1 as set forth in SEQ ID NO:4, (e) a nucleotide sequence containing positions 748 to 791 of SEQ ID NO:1 as set forth in SEQ ID NO:5, (f) a nucleotide sequence containing positions 851 to 961 of SEQ ID NO:1 as set forth in SEQ ID NO:6, (g) a nucleotide sequence containing a functional part of at least 10 contiguous bases of any one of SEQ ID NOs: 1~6 or a combination thereof, and (h) a nucleotide sequence having 90% or more identity to the nucleotide sequence as set forth in any one of SEQ ID NOs: 1~6.

Another embodiment of the disclosures provides a recombinant nucleic acid molecule, which comprises the promoter described herein and a coding sequence operably linked to the promoter.

Yet, another embodiment of the disclosure provides a plant cell and transgenic plant which comprise a recombinant nucleic acid molecule carrying the promoter described herein.

Still, one embodiment of the disclosures provides a method for inducing a gene expression, which comprises a step of providing a plant, plant part or plant cell that comprises a recombinant nucleic acid molecule carrying the promoter described herein, and a step of treating the plant, plant part or plant cell by a stress treatment. The stress treatment comprises a jasmonic acid, jasmonate, sodium chloride, abscisic acid, dehydration or mechanical stress.

Again, another embodiment of the disclosures provides an isolated promoter which comprises a nucleotide sequence selected from the group consisting of: a nucleotide sequence as set forth in any one of SEQ ID NOs: 4~6, a nucleotide sequence containing a functional part of at least 10 contiguous bases of any one of SEQ ID NOs: 4~6 or a combination thereof, and a nucleotide sequence having 90% or more identity to the nucleotide sequence as set forth in any one of SEQ ID NOs: 4~6. The promoter shows a root-specific expression, while the treatment of jasmonic acid or at least one of jasmonates results in the loss of root-specificity but the promoter activity is enhanced.

Further, the embodiment of the disclosures provides an isolated promoter comprising a nucleotide sequence selected from the group consisted of: a nucleotide sequence as set forth in SEQ ID NO: 7, a nucleotide sequence containing a functional part of at least 10 contiguous bases of SEQ ID NO: 7 and a combination thereof, or a nucleotide sequence having 90% or more identity to the nucleotide sequence as set forth in SEQ ID NO: 7. This promoter comprising the nucleotide sequence shows inhibition of an expression of a coding sequence operably linked thereto.

A detailed description is given in the following embodiments with reference to the accompanying drawings.

DESCRIPTION OF THE DRAWINGS

The present invention can be more fully understood by reading the subsequent detailed description and examples with references made to the accompanying drawings, wherein:

FIG. 1 shows the SbUGT promoter at positions −850 to +111 identical to the nucleotide sequence as set forth in SEQ ID NO:1, in which the putative transcription start site is numbered +1 in bold.

FIGS. 2A-2J are a histochemical staining of a GUS expression in transgenic *Arabidopsis* plants (n≥5 for each time point), wherein FIG. 2A is an imbibed seed; FIG. 2B is a 12-hour seedling; FIG. 2C is a 2-day seedling; FIG. 2D is a 6-day seedling; FIG. 2E is a 3-week-old plant; FIG. 2F is a floral bud; FIG. 2G is a flower; FIG. 2H is an early developing silique; and FIG. 2J is a mature silique;

FIG. 6A~6E are a histochemical staining of a GUS expression in transgenic *Arabidopsis* plants harboring the SbP-102U construct at different growth stages (n>30 for each time point), in which FIG. 6A is 2 days of growth; FIG. 6B is 4 days of growth; FIG. 6C is 6 days of growth; FIG. 6D is 8 days of growth; FIG. 6E is 3 weeks of growth.

DETAILED DESCRIPTION

Figure 2J:
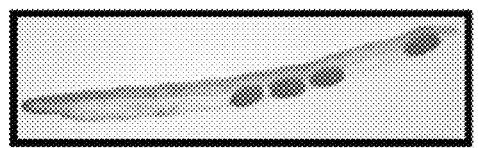

The following description is of the best-contemplated mode of carrying out the invention. This description is made for the purpose of illustrating the general principles of the invention and should not be taken in a limiting sense. The scope of the invention is best determined by reference to the appended claims.

It is noted that some parts of the disclosures has been published on *Planta*. 2010 September; 232 (4):963-974, entitling "Characterization of the *Scutellaria barbata* glycosyltransferase gene and its promoter". It should be understood that terms as used herein have definitions ordinarily used in the art unless otherwise mentioned.

The "promoter" as used herein refers to a genetic element or factor to which RNA polymerase bind to initiate transcription. The promoter regulates the expression of a coding sequence operably linked thereto by initiating transcription. The "promoter activity" as used herein refers to an activity in which transcription is initiated by the promoter acting on RNA polymerase or the like.

The "operably linked" as used herein refers to a link of a nucleotide sequence to a regulatory sequence which activates or regulates the expression of the nucleotide sequence. The "recombinant nucleic acid molecule" as used herein refers to a nucleic acid molecule formed by an artificial conjugation of two or more nucleotide sequences. The method for recombination of a nucleic acid molecule is well known in the art and can be found in "Molecular Cell Biology", Chapter 12. 4th edition. Now York, W. H. Freeman, 2000, for instance.

The "homology" as used herein refers to the magnitude of identity between two or more gene sequences. The homology can be determined by a sequence analyzing tool, such as BLAST and FASTA, comparing the identity of two or more nucleotide sequences.

The "transgenic plant" as used herein refers to a plant carrying a foreign gene. The foreign gene might come from different species, such as plants, animals or microorganisms, etc. A transgenic plant is usually produced by the following steps: isolating a gene sequence of interest, inserting the gene sequence into an expression vector, introducing the expression vector into a host cell by floral dip, electroporation; transfection, agroinfiltration, particle bombardment, etc., and culturing the host cell to form a transgenic plant carrying the gene sequence of interest. The method for producing a transgenic plant can be found in "Characterization of the *Scutellaria barbata* glycosyltransferase gene and its promoter", *Planta*. 2010 September; 232 (4):963-974, for example. The plant for the gene expression is not limited, which may be a tomato, tobacco, or kenaf (*Hibiscus cannabinus* L.), or *Arabidopsis*, or the like. The *Arabidopsis* is preferable due to the well-known genome and short life cycle.

The gene expression according to the invention comprises a stable or transient expression. The stable expression refers to a production of recombinant proteins by integrating the gene of interest into the chromosome of the host cell. The transient expression refers to a temporary expression of a foreign gene in the target cell over a relatively brief time span, in which the foreign gene may not integrate into the host chromosome and pass onto the next generation.

The "enhance" or "enhancement" as used herein refers to an increase of a gene expression. The "inhibit" or "inhibition" as used herein refers to a decrease or elimination of a gene expression. In one embodiment of the invention, the gene expression is observed by a histochemical assay or by fluorometric quantification.

In the disclosures, cloning is not specifically limited and the procedure commonly used in the art may be adopted. For example, a DNA sequence of interest is amplified by a polymerase chain reaction (PCR) and digested by restriction enzymes to form several fragments. The fragments are separated by gel electrophoresis. In addition, a DNA fragment was isolated and fused to an expression vector at the restriction site or the end of the DNA fragment. The expression vector is then transformed into a host cell, and the DNA fragment of interest is cloned through the host cell reproduction.

In one embodiment of the invention, a pBI121 binary plasmid is used as the expression vector for identifying the activity of the promoter. More specific, the CaMV35S promoter of the pBI121 binary plasmid is substituted with the promoter of the invention, and β-glucuronidase (GUS), adjacent to the downstream of the CaMV35S promoter in the pBI121 binary plasmid, is used for a reporter gene to identify the activity of the promoter of the invention.

Thereafter, the expression vector is further transformed into a plant host cell to evaluate the expression of the reporter sequence in different organs and tissues. The method for transformation is not limited in the invention, which might be floral dip, electroporation, transfection, agroinfiltration, particle bombardment, or the like. Agroinfiltration is a method of transformation by introducing an expression vector into an *Agrobacterium* DNA and injecting the *Agrobacterium* to a plant (usually leaves). Due to a fast gene expression and simple operation, agroinfiltration is a useful method for observing gene activity or expression.

Figure 1:
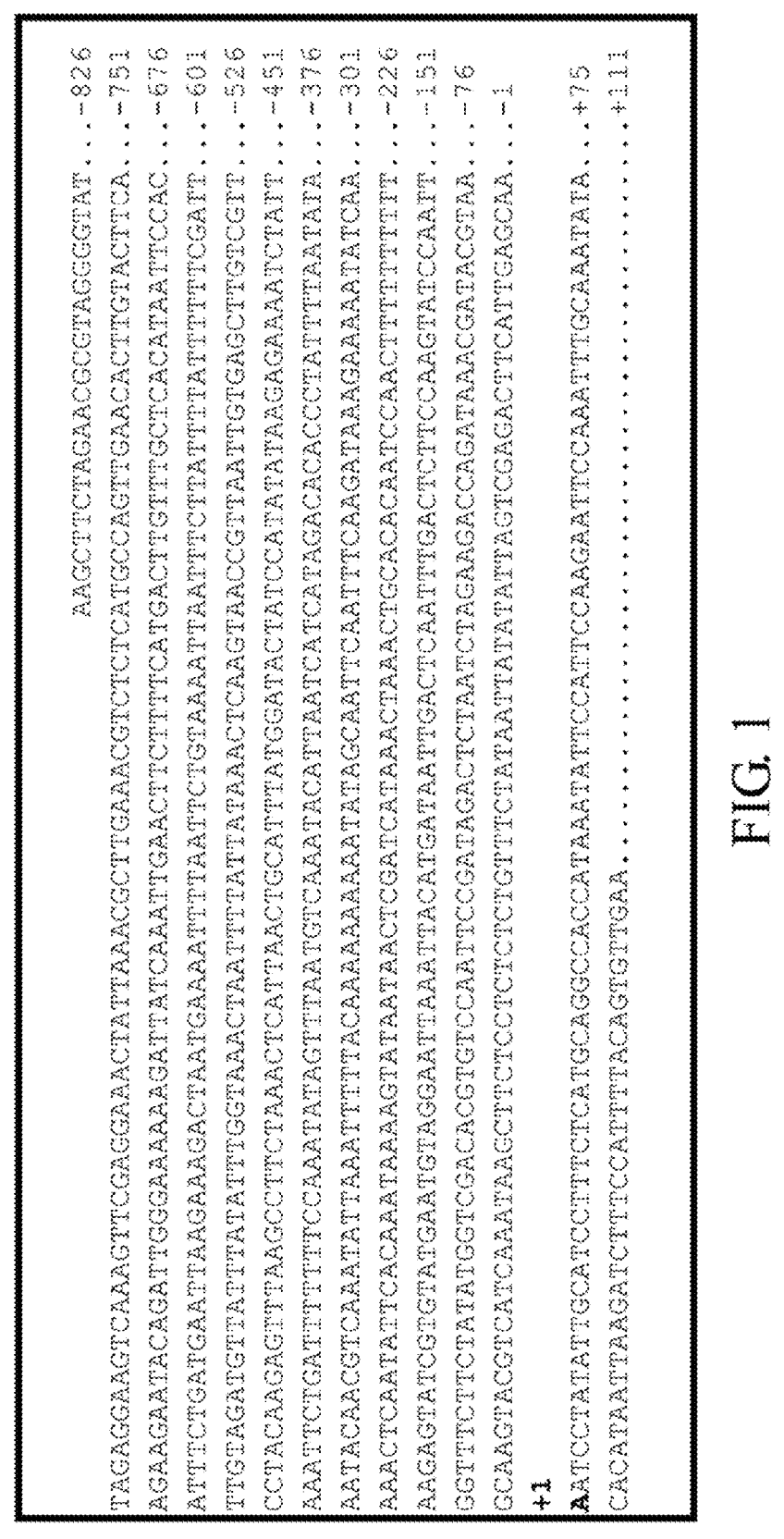

The promoter in one embodiment of the invention is isolated from the 5'-flanking region of the gene encoding glycoyltransferase of *Scutellaria barbata*. The length of the promoter with the 5'-UTR is 961 bp as shown in FIG. 1. As the transcription start site is numbered +1 in bold, the promoter with the important regulatory sequence spans from positions −850 to +111 (FIG. 1).

Relatively, the nucleotide sequence at positions −850 to +111 of the promoter in FIG. 1 is identical to the nucleotide sequence as set forth in SEQ ID NO: 1. As the promoter has a deletion at positions −850 to −393 and +1 to +111 respectively corresponding to positions 1 to 457 and 851 to 961 of SEQ ID NO: 1, the nucleotide sequence is identical to the nucleotide sequence as set forth in SEQ ID NO: 2. Meanwhile, as the promoter has a deletion at positions −850 to −393, −237 to −176 and +1 to +111 respectively corresponding to positions 1 to 457, 613 to 674 and 851 to 961 of SEQ ID NO: 1, the nucleotide sequence is identical to the nucleotide sequence as set forth in SEQ ID NO: 3.

Figure 5:
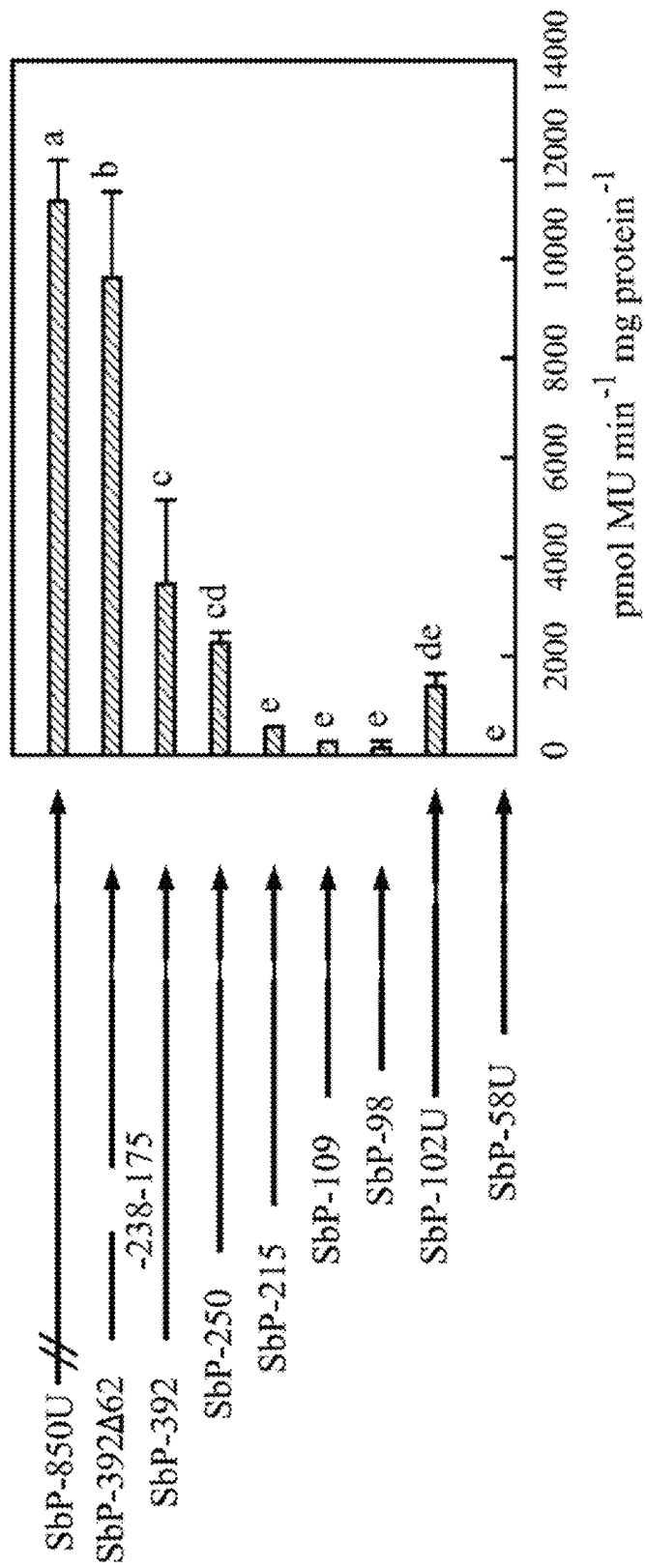
FIG. 5 is a quantitative analysis of GUS activity of the transgenic *Arabidopsis* plant harboring deletion constructs of the SbUGT promoter, wherein the letter following each column shows a significant difference based on the Fisher's least significant difference test (p<0.05)

According to the deletion analyses, when the promoter deletes at positions −850 to −393 and +1 to +111 or at positions −850 to −393, −237 to −176 and +1 to +111, the activity of the promoter to initiate transcription is not greatly reduced (FIG. 5).

However, when the promoter has a deletion at positions −850 to −103 corresponding to positions 1 to 747 of SEQ ID NO: 1, the nucleotide sequence is identical to the nucleotide sequence as set forth in SEQ ID NO: 4. The inventors reveal that the promoter having a deletion at positions −850 to −103 (SEQ ID NO: 4), not only shows the promoter activity but regulates tissue-specific expression of the reporter gene. The tissue-specific expression occurs in the root of the plant. The "root specificity" or "root-specific" as used herein refers to the expression of a coding gene accumulating in the root of the plant.

The inventors further disclose that the nucleotide sequence at positions −102 to −59 and the 5'-UTR at positions +1 to +111 are the essential fragments for the root-specific expression. Relatively, the nucleotide sequence at positions −102 to −59 of the promoter is correspondent to the nucleotide sequence at positions 748 to 791 of SEQ ID NO: 1, which is identical to the nucleotide sequence as set forth in SEQ ID NO: 5. The nucleotide sequence at positions +1 to +111 of the promoter correspondent to the nucleotide sequence at positions 851 to 961 of SEQ ID NO: 1 is identical to the nucleotide sequence as set forth in SEQ ID NO: 6.

Comparing the expression of the reporter gene, the promoter containing a deletion at positions −237 to −176 regulates higher gene expression than the promoter with a deletion at positions −850 to −393 (SEQ ID NO: 2). Accordingly, it is suggested that the nucleotide sequence at positions −237 to −176 may have activity to inhibit the expression of the coding gene. Relatively, the nucleotide sequence at positions −237 to −176 of the promoter correspondent to positions 613 to 674 of SEQ ID NO: 1 is identical to the nucleotide sequence as set forth in SEQ ID NO: 7.

The promoter of the invention further contains a nucleotide sequence comprising a functional part of at least 10 contiguous bases of any one of SEQ ID NOs: 1~7 or a combination thereof. The "functional part" as used herein refers to the nucleotide sequence having the same function as any one of SEQ ID NOs: 1~7, i.e. promoter activity. The functional part may have 10~40 contiguous bases and preferably 10~60 contiguous bases. Combinations of two or more non-contiguous functional parts are also included in the application.

The promoter of the invention further comprises a nucleotide sequence having 90% or more identity to the nucleotide sequence as set forth in any one of SEQ ID NOs: 1~7 and possesses the promoter activity like any one of SEQ ID NOs: 1~7. More specific, the nucleotide sequence as set forth in any one of SEQ ID NOs: 1~7 might have one or more nucleotides which is added, deleted, substituted, and/or inserted thereto. The nucleotide sequence preferably has 92%, 95%, 98%, 99% or 100% identity to any one of SEQ ID NOs: 1~7. Furthermore, the promoter of the invention comprises a nucleotide sequence having 92%, 95%, 98%, 99% or 100% identity to the nucleotide sequence comprising a functional part of at least 10 contiguous bases of any one of SEQ ID NOs: 1~7, provided that the nucleotide sequence has the activity of the promoter.

The promoter activity of the invention can be further induced by a stress treatment. The "stress treatment" as used herein refers to a treatment by a factor which affects the growth of a normal plant, for example, high temperature, salts, dehydration, pathogen or mechanical stresses, etc. In one embodiment, the stress treatment comprises jasmonic acid, at least one of jasmonates, sodium chloride (NaCl), or abscisic acid (ABA) to treat the plant. The jasmonates may comprise methyl jasmonate (MeJA). Dehydration and mechanical stresses are also used as the stress treatment to induce the expression of the reporter gene.

The concentration or strength of the stress treatment is not limited, as long as it affects the plant growth. A person skilled in the art may adjust the concentration or strength of the stress treatment according to the growth condition of the plant and a routine experiment. For instance, the stress treatment may use 100 μM MeJA, 250 mM NaCl or 100 μM ABA.

The transgenic plant containing the nucleotide sequence at positions −850 to +111 of the promoter shows high expression of the reporter gene in the leaves. When the transgenic plant carries a deletion at positions −850 to −103 of the promoter (SEQ ID NO: 4), the expression of the reporter gene is enhanced in the root, showing root specificity (FIG. 6A~6E). However, after a treatment of MeJA, the expression of the reporter gene is observed both at the aerial part and root (whole plant), resulting in the loss of the root specificity. It is noted that no study or research shows that root specificity in nature would be lost after the treatment of the inducer, MeJA.

It is known that most of herbal medicines have active ingredients in the root. The root specificity disclosed in the invention may effectively produce the active ingredients of the herbal medicines.

In one embodiment of the invention, the promoter can operably link to a coding sequence encoding glycosyltransferase or β-glucuronidase (GUS) or link to a foreign gene which is not linked to the promoter in the nature. The promoter regulates the expression of the coding sequence or foreign gene.

Therefore, the promoter of the invention can be appropriately designed by transgenic genetic engineering to efficiently improve the production of crops, biofuels, or the like in the agricultural industry. For example, oil producing plants might increase oil production for biodiesel, or plants may have an ability against pathogens, drought or salty soils, etc. to increase the production of crops, by the regulation of the promoter.

EXAMPLES

Example 1

Cloning of the SbUGT Gene

Total cellular RNA was isolated from a whole *S. barbata* plant using a modified hexadecyltrimethylammonium bromide (CTAB) method [Chen et al. (2007) MeJA-induced transcriptional changes in adventitious roots of *Bupleurum Kaoi*. Plant Sci 173:12-24]. A partial cDNA of the gene encoding glycosyltransferases (SbUGT) was obtained with reverse transcription PCR using a SuperScript™ III Reverse Transcriptase Kit (Invitrogen, Carlsbad, Calif., USA) with a pair of degenerate primers (SEQ ID NOs: 8, 9) designed according to the sequence of *S. baicalensis* 7-O-UGT (accession number: BAA83484) [Hirotani et al. (2000) Cloning and expression of UDP-glucose: flavonoid 7-O-glucosyltransferase from hairy root cultures of *Scutellaria baicalensis*. Planta 210: 1006-1013.

The 5'- and 3'-rapid amplification of the cDNA ends (RACE) PCR with the SMART RACE cDNA Amplification Kit (BD Biosciences Clontech, Palo Alto, Calif., USA) were used to generate a full-length cDNA based on the sequence of the partial SbUGT cDNA (SEQ ID NOs: 10, 11) and according to the manufacturer's procedures. The resulting cDNA was sequenced. A sequence similarity search was performed against the nucleotide database (GenBank) using the BLAST algorithm.

Cloning of the SbUGT Promoter

The 5'-flanking region of the SbUGT was obtained using the Universal GenomeWalker Kit (Clontech). After digestion with XbaI and StuI, partially purified DNA was ligated to the GenomeWalker Adaptor. A first-round PCR was performed using Adaptor Primer 1 (SEQ ID NO: 12) and a deigned primer SbP-GSP1 (SEQ ID NO: 13), which was complementary to the proximal 5'-coding region of the SbUGT gene (+119 to +145).

The amplified product was subjected to a second round of PCR using the nested Adaptor Primer 2 (SEQ ID NO: 14) and a nested-specific primer SbP-GSP2 (SEQ ID NO: 15).

The PCR product was cloned into a pCR2.1-TOPO TA vector (Invitrogen) to generate the promoter of *S. barbata* (pCR-SbP) and was sequenced. The transcription start site was predicted using alignment matrices from the PlantProm DB database [Shahmuradov et al. (2003) PlantProm DB: a database of plant promoter sequences. *Nucleic Acids Res* 31:114-117] together with a comparison of sequences obtained from the '-RACE-PCR.

A pCR-SbP construct was excised with BglII and HindIII and inserted into a binary vector pBI121 between the BamHI and HindIII sites to replace the CaMV35S promoter and fused to the β-glucuronidase (GUS) coding sequence, which constructed the SbP-850U (FIG. 1). SbP-102U and SbP-98U constructs were generated from the SbP-850U digested with the XbaI and HindII, respectively, and then self-ligated.

A homology search for putative cis-acting elements was performed with the PlantCARE [Lescot et al. (2002) PlantCARE, a database of plant cis-acting regulatory elements and a portal to tool for in silico analysis of promoter sequences. *Nucleic Acids Res* 30:325-327] and PLACE [Higo et al. (1999) Plant cis-acting regulatory DNA elements (PLACE) database. *Nucleic Acids Res* 27:297-300] databases.

Construction of the SbUGT Promoter with 5'-Deletions

A series of 5'-deletion fragments of the SbUGT promoter were generated with pairs of forward primers containing a SbfI site (SEQ ID NOs: 16~19) and reverse primers containing a BamHI site (SEQ ID NO: 20). The amplified fragments were cloned in the pCR2.1-TOPO TA vector to form constructs pCR-109, pCR-215, pCR-250 and pCR-392. Construct pCR-392Δ62 was produced from pCR-392 with a 62-bp deletion (−237 to −176) by PCR amplification with the primer (SEQ ID NOs: 21~22). The fragment of the SbUGT promoter for each construct and the primers used therefore are listed in Table 1.

TABLE 1

| Construct | The fragment of the SbUGT promoter (nucleotide position) | Primer |
| --- | --- | --- |
| pCR-109 | −108 to +111 | Forward: SEQ ID NO: 16 |
| | | Reverse: SEQ ID NO: 20 |
| pCR-215 | −214 to +111 | Forward: SEQ ID NO: 17 |
| | | Reverse: SEQ ID NO: 20 |
| pCR-250 | −249 to +111 | Forward: SEQ ID NO: 18 |
| | | Reverse: SEQ ID NO: 20 |
| pCR-392 | −391 to +111 | Forward: SEQ ID NO: 19 |
| | | Reverse: SEQ ID NO: 20 |
| pCR-392Δ62 | −240 to −228 and | SEQ ID NO: 21 |
| | −177 to −167 | SEQ ID NO: 22 |

After confirmation with double-stranded sequencing, each of the inserts containing different regions of the SbUGT promoter was excised with the SbfI and BamHI, cloned separately into the binary vector pBI121 [Jefferson et al. (1987) GUS fusions: beta-glucuronidase as a sensitive and versatile gene fusion marker in higher plants. *EMBO J.* 6:3901-3907] between the PstI and BamHI sites to replace the CaMV35S promoter and fuse to the GUS coding sequence.

All the constructs carrying various regions of the SbUGT promoter in the pBI121 plasmid were confirmed with sequencing. The pBI121 vector containing the GUS gene driven by the CaMV35S promoter was used as a positive control.

Plant Transformation

The constructs containing different regions of the SbUGT promoter fused to the GUS gene were introduced into the *Agrobacterium tumefaciens* LBA4404 by electroporation and the *agrobacterium*-mediated transformation of *Arabidopsis* was conducted with the floral dip method [Clough S J (2005) Floral dip: *Agrobacterium*-mediated germ line transformation. *Methods Mol Biol* 286:91-102].

After transformation, seeds of the *Arabidopsis* were sterilized as previously described and then grown on a ½ MS medium supplemented with 250 mg/L of carbenicillin and 100 mg/L of kanamycin for selection. The transgenic plants were verified with PCR using a primer pair (forward primer: SEQ ID NO: 23, reverse primer: SEQ ID NO: 24) matching sequences in the pBI121. The T3 homozygous transgenic plants were used for promoter analyses.

Fluorometric Quantification of GUS Activity and Histochemical Staining

Fluorometric GUS assays were performed to analyze crude plant extracts as described by Jefferson et al. [Jefferson et al. (1987) GUS fusions: beta-glucuronidase as a sensitive and versatile gene fusion marker in higher plants. *EMBO J.* 6:3901-3907].

Each sample was grounded to a fine powder in liquid nitrogen in an Eppendorf tube. A volume of 0.4 mL of a GUS extraction buffer containing 50 mM of sodium phosphate (pH 7.0), 5% of glycerol, 0.1% of Triton X-100, 0.1% of 2-mercaptoethnol and 0.1% of sodium lauryl sarcosine was added and vortexed. The supernatant was collected after centrifugation at 16,000 g for 10 min at 4° C. The GUS activity of each sample was assayed using 200 μL reaction buffer containing 50 mM sodium phosphate (pH 7.0), 0.1% Triton X-100, 2 mM DTT, 0.1% 2-mercaptoethanol and 1 mM 4-methylumbelliferyl-β-D-glucuronide (4-MUG), and was expressed as pmol of 4-methylumbelliferone (MU) per min per mg protein. The total protein content was determined using the Bradford method.

Histochemical localization of the GUS activity was performed according to the method described by Blázquez et al. [Blázquez et al. (1997) LEAFY expression and flower initiation in *Arabidopsis*. *Development* 124:3835-3844] with minor modifications. The plant was stained in a solution consisting of 100 mM sodium phosphate (pH 7.0), 0.1% Triton X-100, 0.5 mM $K_3[Fe(CN)_6]$, 0.5 mM $K_4[Fe(CN)_6]$, 10 mM $Na_2EDTA$, 10% methanol and 0.5 mM 5-bromo-4-chloro-3-indolyl-β-glucuronide (X-Gluc), followed by 30 min of vacuum infiltration and then incubation at 37° C. for 24 hours. After removing chlorophyll with 70% ethanol, examination and photography were performed with a dissecting microscope (Leica, Wetzlar, Germany) and a DGIS-8 Digital Gel Image System (TopBio Co., Taipei, Taiwan).

The GUS activity in the transgenic *Arabidopsis* carrying the SbP-850U (positions −850 to +111) by histochemical assay was shown in imbed seeds (FIG. 2A) and 12-hour (FIG. 2B), 2-day (FIG. 2C), and 6-day (FIG. 2D) seedlings. Strong GUS staining (the dark black) was exhibited at the meristems of the apical shoots, roots and vascular tissues of the seedling.

Figure 2I:
Figure 2H:
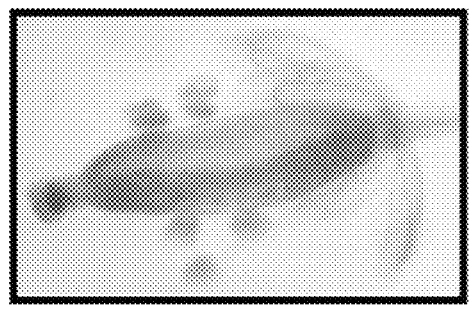
Figure 2G:
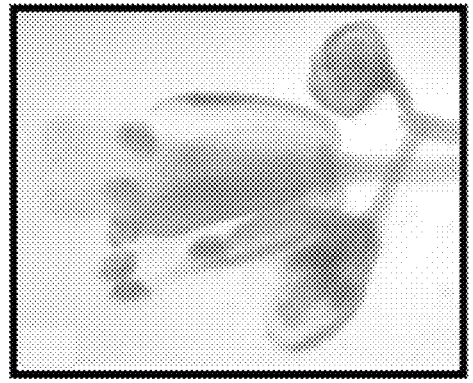
Figure 2F:
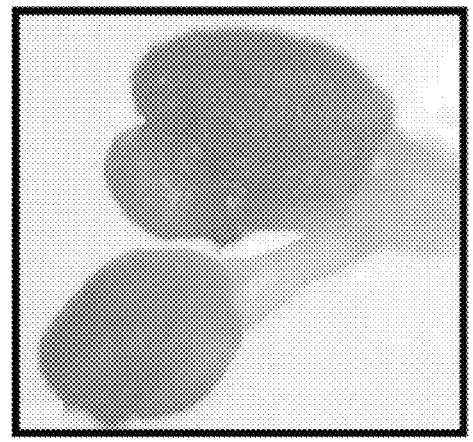

The expression of the GUS gene remained high in the 3-week-old transgenic plant (FIG. 2E). In the 2-month-old transgenic plant, the GUS staining was detected in the leaves, roots sepals (FIG. 2F, 2G), developing siliques and seeds (FIGS. 2H, 2I and 2J). No GUS staining was observed in the anthers (FIG. 2G, 2H).

Figure 3:
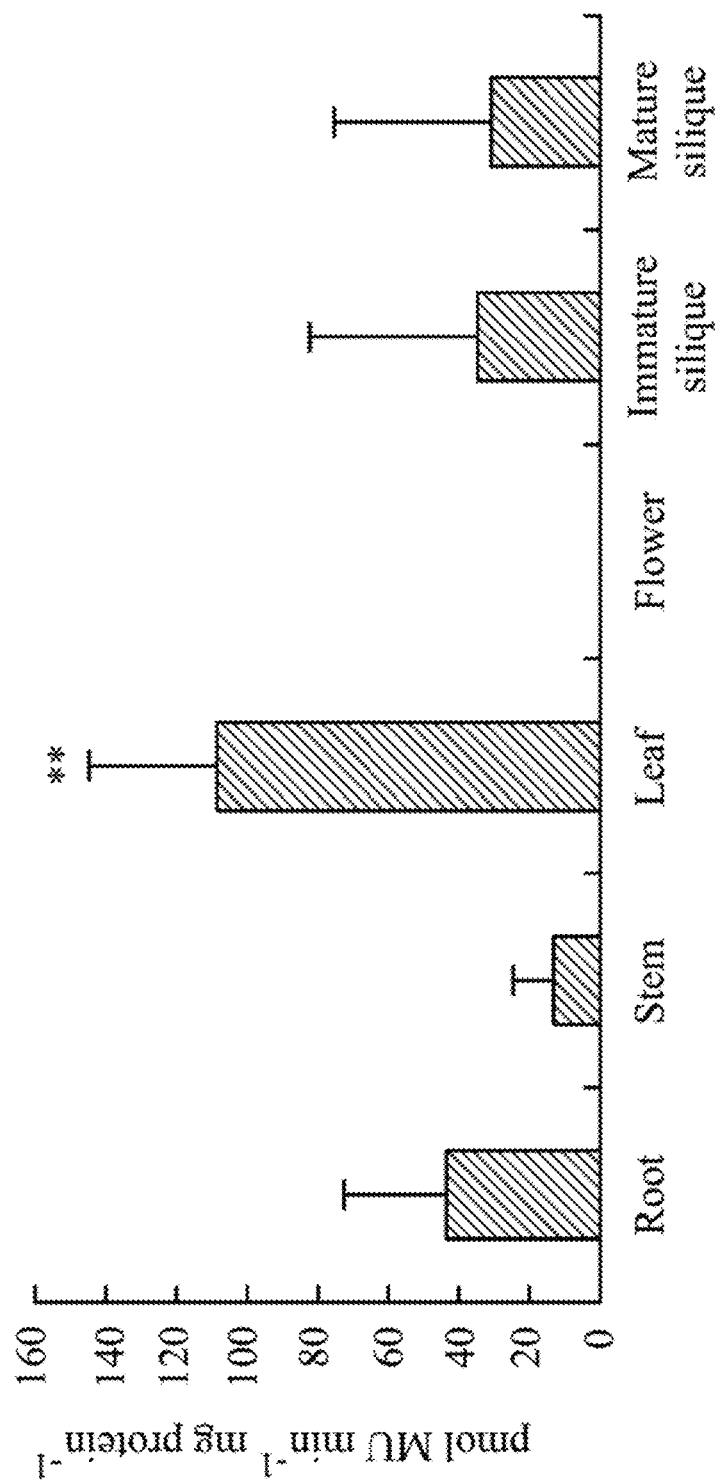
FIG. 3 is the GUS expression in different organs of 2-month-old transgenic *Arabidopsis* plants harboring a SbP-850U construct, wherein the error bars indicate the SD of the mean (n=3) and the double asterisks indicate a significant difference at p<0.01.

The fluorometric analysis to the 2-month-old transgenic plant carrying the SbP-850U promoter and the GUS coding gene showed consistent results with that of the histochemical analyses. One-way ANOVA indicated that the leaves had significantly higher GUS expression than other examined tissues ($p<0.05$) (FIG. 3). Leaves of the transgenic plants displayed a GUS activity level of about 2.5-times higher than that of roots. Low GUS activity was found in the stems and flowers.

Stress Treatment

To analyze the activity of different promoter fragments, the transgenic plants carrying the deletion constructs were harvested for fluorometric assay.

3-week-old transgenic plants *Arabidopsis* carrying the SbP-850U construct were transferred into a 6-well plate containing a ½MS medium supplemented with 100 µM MeJA, 250 mM NaCl or 100 µM ABA for 6 hours. The control sample was subjected to the medium without any treatment. The dehydration sample was treated with no medium.

The 2-week-old transgenic plants harboring the SbP-102U construct were transferred to the ½ MS medium alone or supplemented with 100 µM MeJA in a 6-well plate for 6 hours for fluorometric assay and GUS staining.

Discussion

Figure 4:
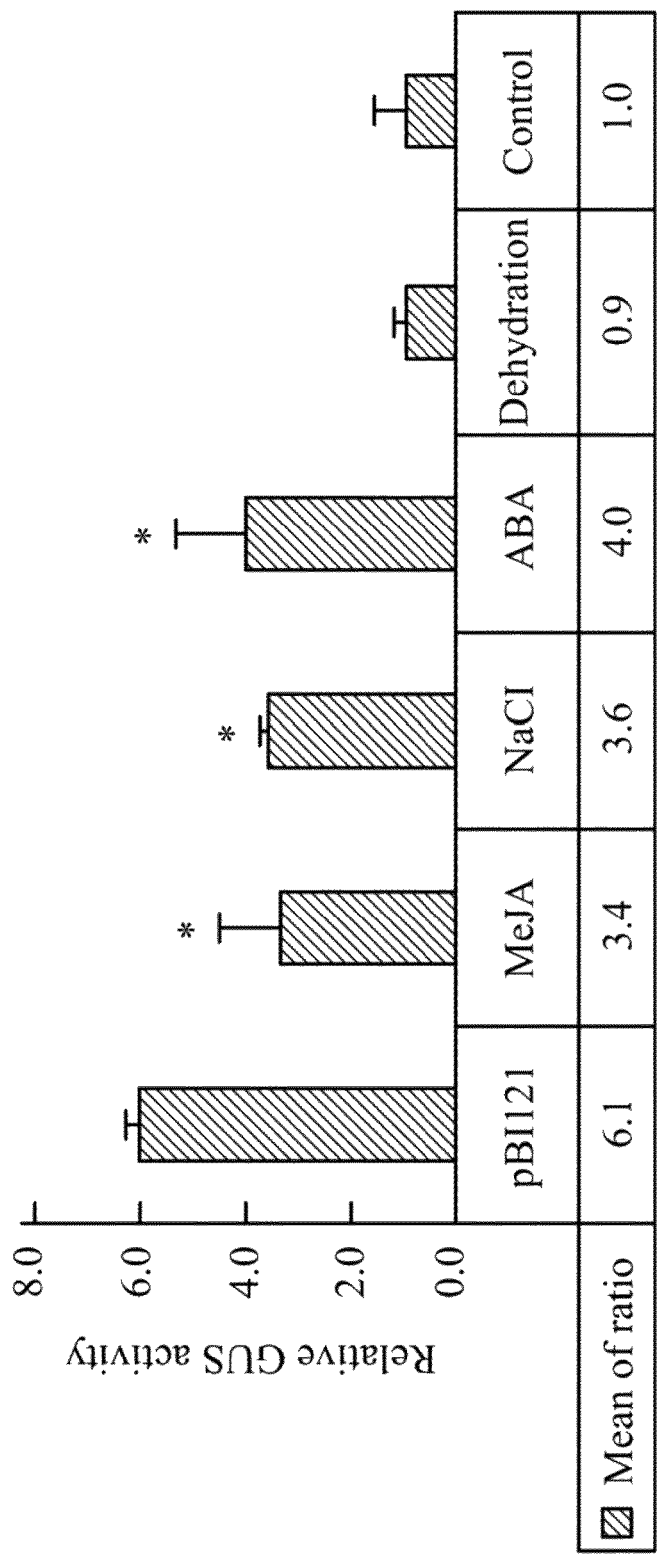
FIG. 4 is a relative GUS activity in a transgenic *Arabidopsis* plant harboring a SbP-850U construct (determined by a quantitative MUG assay), in which the control shows the activity of untreated plants, the error bar indicates the SD of the mean (n=3), and the asterisk indicates a significant difference at p<0.05.

As shown in FIG. 4, the GUS expression in the transgenic plant *Arabidopsis* carrying the SbP-850U construct was significantly increased by the treatment of NaCl (about 3.6-fold), MeJA (about 3.4-fold) and ABA (about 4-fold) ($p<0.05$) based on the control.

In order to find regulatory regions that are important for the SbUGT promoter activity, 9 different 5'-flanking DNA fragments were fused to the GUS gene. The quantitative analyses of the GUS activity of the transgenic plants ($n≥5$) is shown in FIG. 5 by a one way-ANOVA, in which the SbP-850U refers to the construct carrying the SbUGT promoter at position −850 to +111, the SbP-392Δ62 refers to a deletion at position −850 to −393, −237 to −176 and +1 to +111 of the SbP-850U construct, the SbP-392 refers to a deletion at positions −850 to −393 and +1 to +111 of the SbP-850U construct, the SbP-250 refers to a deletion at positions −850 to −251 and +1 to +111 of the SbP-850U construct, the SbP-215 refers to a deletion at positions −850 to −215 and +1 to +111 of the SbP-850U construct, the SbP-109 refers to a deletion at positions −850 to −110 and +1 to +111 of the SbP-850U construct, the SbP-98 refers to a deletion at positions −850 to −99 and +1 to +111 of the SbP-850U construct, the SbP-102U refers to a deletion at positions −850 to −103 of the SbP-850U construct, and the SbP-58U refers to a deletion at positions −850 to −59 and +1 to +111 of the SbP-850U construct.

FIG. 5 revealed that a 215-bp fragment proximate to the transcription start site (+1) was sufficient to drive the basal GUS expression in the plant. According to the results, the plant carrying the SbP-850U construct exhibited the highest GUS activity, while the deletion decreased the GUS expression level. The GUS expression level in the SbP-392, SbP-250 and SbP-215 transgenic plants decreased to 30%, 20% and 4% of that in the SbP-850U plant, respectively. It was suggested that important regulatory elements were present at positions −250 to −215 of the promoter.

It was also revealed that the GUS expression in the SbP-109 and SbP-98 transgenic plants was almost undetectable. However, GUS activity in the SbP-392Δ62 plant was about 2.9-times higher than that of the SbP-392 plant ($p<0.01$). It was suggested that some putative suppressor binding sites may exist at positions −237 to −176. Accordingly, it is suggested that certain negative regulatory factors may be in the present of positions −237 to −215 and certain positive regulatory factors may exist at positions −392 to −251.

The GUS expression in the SbP-109 and SbP-58U plants was barely detectable, while that in the SbP-102U plant was specifically showed in the root (FIG. 6A-6E). The results were in agreement with the increasing evidence that discrete promoter domains may contribute to gene expression in different tissue types through complicated interactions of factors between distal/proximal elements in the promoter and the downstream untranslated region of the 5'-flanking regions [Waclawovsky A J, et al. (2006) Combinatorial regulation modules on GmSBP2 promoter: a distal cis-regulatory domain confines the SBP2 promoter activity to the vascular tissue in vegetative organs. *Biochim Biophys Acta* 1759:89-98; Lang Z., et al. (2008) Functional characterization of the pollen-specific SBgLR promoter from potato (*Solanum tuberosum* L.). *Planta* 22:387-396]. Therefore, the cooperation of sequences at positions −102 to −59 and +1 to +111 plays an essential role in the root-specific expression.

Figure 6A:
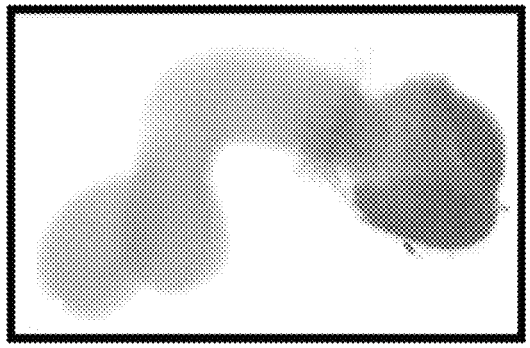
Figure 6B:
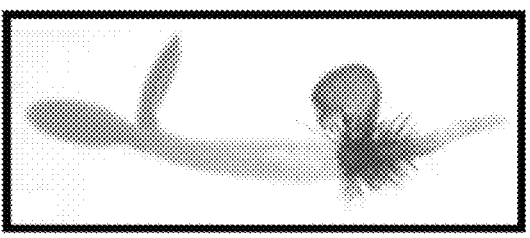
Figure 6C:
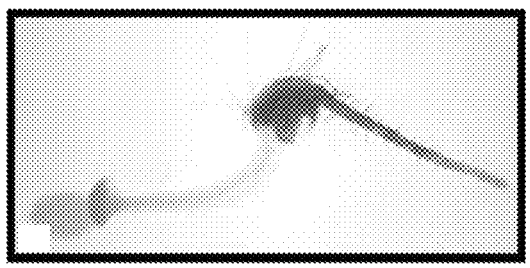
Figure 6D:
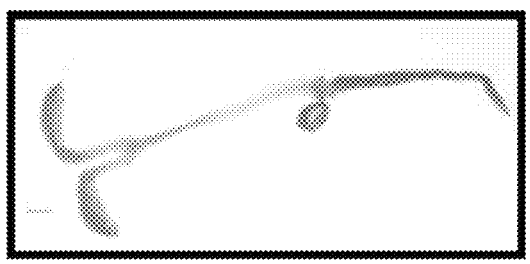
Figure 6E:
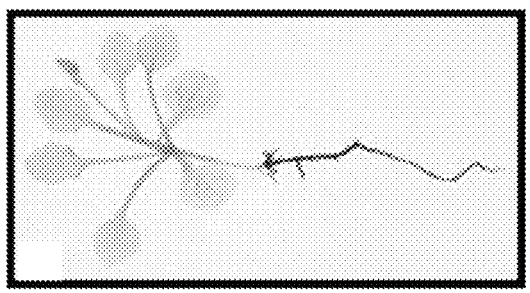

The GUS expression level in the SbP-102U plants was about 12% of that in the plant. However, the GUS expression in the SbP-102U plants was accumulated in the root after the SbP-102U plants were further investigated during development from 2 days to 3 weeks of growth (FIG. 6A−6E). GUS activity in the SbP-850U transgenic plant was mainly detected in the aerial part (Table 2), whereas the activity in the SbP-102U plant was localized in the root (Table 2, FIG. 7). The results indicated that positive and negative regulatory elements involved in organ/tissue specificity may coexist in the SbUGT promoter.

TABLE 2

Comparison of GUS activity (pmol MU min$^{-1}$ mg protein$^{-1}$) of 3-week-old and 5-week-old transgenic *Arabidopsis* plants carrying pBI121, SbP-850U and SbP-102U constructs

| Construct | 3-week-old | | 5-week-old | |
|---|---|---|---|---|
| | Aerial part | Root | Aerial part | Root |
| pBI121 | 5,942 ± 2,971 | 3,225 ± 2,380 | 11,928 ± 1,453 | 5,420 ± 2,698 |
| SbP-850U | 2,662 ± 1,476 | 275 ± 208 | 2,361 ± 781 | 182 ± 67 |
| SbP-102U | 34 ± 22 | 509 ± 328 | 27 ± 15 | 352 ± 203 |

Data are shown as mean ± SD (n = 5)

Figure 7:
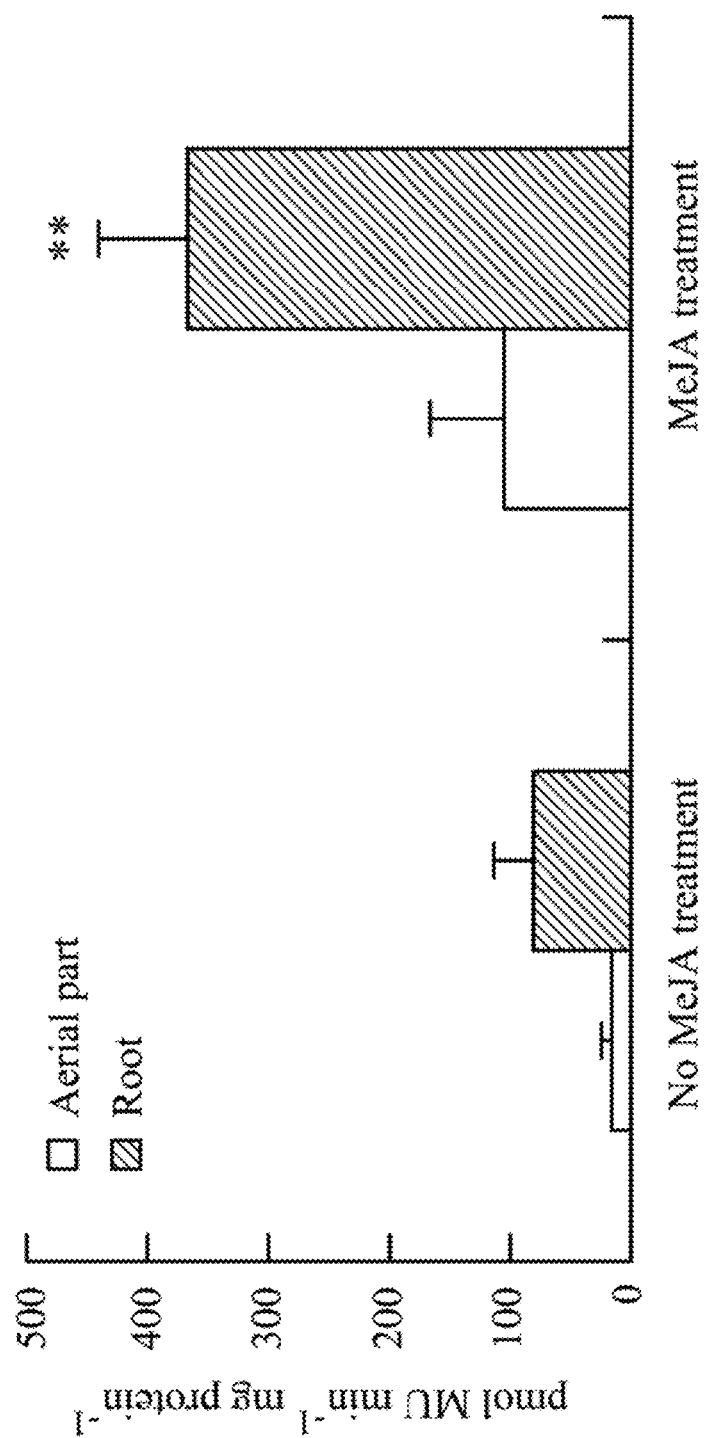
FIG. 7 is the GUS expression of the 2-week-old transgenic *Arabidopsis* plant harboring a construct SbP-102U under a methyl jasmonate treatment, wherein each bar represents the mean±SD (n=6) and the double asterisks represent a significant difference (p<0.01).

To further study the root specificity of the SbP-102U construct, the transgenic plant carrying SbP-102U construct was grown under stress treatments. 2-week-old seedlings were treated with 100 μM MeJA, indicating that MeJA significantly enhanced GUS expression in the root ($p<0.001$) and induced GUS expression in the aerial part ($p<0.05$) (FIG. 7). In other words, the root specificity of the SbP-102U construct disappeared due to the treatment of MeJA, while the promoter activity is enhanced by application of methyl jasmonate.

While the invention has been described by way of example and in terms of the preferred embodiments, it is to be understood that the invention is not limited to the disclosed embodiments. To the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. An isolated promoter, comprising a nucleotide sequence selected from the group consisting of:
   (a) the nucleotide sequence as set forth in SEQ ID NO:1,
   (b) the nucleotide sequence containing the deletion at positions 1 to 457 and 851-961 of SEQ ID NO:1,
   (c) the nucleotide sequence containing the deletion at positions 1 to 457, 613 to 674 and 851-961 of SEQ ID NO:1,
   (d) the nucleotide sequence containing deletion at positions 1 to 747 of SEQ ID NO:1,
   (e) the nucleotide sequence at positions 748 to 791 of SEQ ID NO:1, and
   (f) the nucleotide sequence at positions 851 to 961 of SEQ ID NO:1; wherein said promoter is linked to a heterologous nucleotide sequence.

2. A recombinant nucleic acid molecule, comprising a promoter and a coding sequence operably linked to the promoter, wherein the promoter comprises a nucleotide sequence selected from the group consisting of:
   (a) the nucleotide sequence as set forth in SEQ ID NO:1,
   (b) the nucleotide sequence containing the deletion at positions 1 to 457 and 851-961 of SEQ ID NO:1,
   (c) the nucleotide sequence containing the deletion at positions 1 to 457, 613 to 674 and 851-961 of SEQ ID NO:1,
   (d) the nucleotide sequence containing the deletion at positions 1 to 747 of SEQ ID NO:1,
   (e) the nucleotide sequence at positions 748 to 791 of SEQ ID NO:1, and
   (f) the nucleotide sequence at positions 851 to 961 of SEQ ID NO:1; wherein said promoter is linked to a heterologous nucleotide sequence.

3. The recombinant nucleic acid molecule as claimed in claim 2, wherein the coding sequence is stably or transiently expressed.

4. The recombinant nucleic acid molecule as claimed in claim 2, wherein the promoter enhances the coding sequence expression.

5. The recombinant nucleic acid molecule as claimed in claim 2, wherein the coding sequence comprises a nucleotide sequence encoding glycosyltransferase, a reporter gene or a foreign gene.

6. The recombinant nucleic acid molecule as claimed in claim 2, wherein a stress treatment induces the coding sequence expression.

7. The recombinant nucleic acid molecule as claimed in claim 6, wherein the stress treatment comprises a jasmonic acid, jasmonate, sodium chloride, abscisic acid, dehydration or mechanical stress.

8. The recombinant nucleic acid molecule as claimed in claim 2, wherein the coding sequence comprising a nucleotide sequence selected from the group consisting of: the nucleotide sequence as set forth in SEQ ID NOs: 4-6 is root-specific expression.

9. A plant cell, comprising a promoter and a heterologous coding sequence operably linked to the promoter, wherein the promoter comprises a nucleotide sequence selected from the group consisting of:
   (a) the nucleotide sequence as set forth in SEQ ID NO:1,
   (b) the nucleotide sequence containing the deletion at positions 1 to 457 and 851-961 of SEQ ID NO:1,
   (c) the nucleotide sequence containing the deletion at positions 1 to 457, 613 to 674 and 851-961 of SEQ ID NO:1,
   (d) the nucleotide sequence containing the deletion at positions 1 to 747 of SEQ ID NO:1,
   (e) the nucleotide sequence at positions 748 to 791 of SEQ ID NO:1, and
   (f) the nucleotide sequence at positions 851 to 961 of SEQ ID NO:1.

10. The plant cell as claimed in claim 9, wherein the coding sequence is stably or transiently expressed.

11. The plant cell as claimed in claim 9, wherein the promoter enhances the coding sequence expression.

12. The plant cell as claimed in claim 9, wherein the coding sequence comprises a nucleotide sequence encoding glycosyltransferase, a reporter gene or a foreign gene.

13. The plant cell as claimed in claim 9, wherein a stress treatment induces the coding sequence expression.

14. The plant cell as claimed in claim 13, wherein the stress treatment comprises a jasmonic acid, jasmonate, sodium chloride, abscisic acid, dehydration or mechanical stress.

15. The plant cell as claimed in claim 9, wherein the coding sequence comprising a nucleotide sequence selected from the group consisting of: the nucleotide sequence as set forth in SEQ ID NOs: 4-6 is root-specific expression.

16. A transgenic plant, comprising a cell containing a recombinant nucleic acid molecule, wherein the recombinant nucleic acid molecule comprises a promoter and a coding sequence operably linked to the promoter, and wherein the promoter comprises a nucleotide sequence selected from the group consisting of:
   (a) the nucleotide sequence as set forth in SEQ ID NO:1,
   (b) the nucleotide sequence containing the deletion at positions 1 to 457 and 851-961 of SEQ ID NO:1,
   (c) the nucleotide sequence containing the deletion at positions 1 to 457, 613 to 674 and 851-961 of SEQ ID NO:1,
   (d) the nucleotide sequence containing the deletion at positions 1 to 747 of SEQ ID NO:1,
   (e) the nucleotide sequence at positions 748 to 791 of SEQ ID NO:1, and
   (f) the nucleotide sequence at positions 851 to 961 of SEQ ID NO: 1.

17. The transgenic plant as claimed in claim 16, wherein the coding sequence is stably or transiently expressed.

18. The transgenic plant as claimed in claim 16, wherein the promoter enhances the coding sequence expression.

19. The transgenic plant as claimed in claim 16, wherein the coding sequence comprises a nucleotide sequence encoding glycosyltransferase, a reporter gene or a foreign gene.

20. The transgenic plant as claimed in claim 16, wherein a stress treatment induces the coding sequence expression.

21. The transgenic plant as claimed in claim 20, wherein the stress treatment comprises a jasmonic acid, jasmonate, sodium chloride, abscisic acid, dehydration or mechanical stress.

22. The transgenic plant as claimed in claim 16, wherein the transgenic plant is selected from the group consisting of a tomato, tobacco, kenaf or *Arabidopsis*.

23. The transgenic plant as claimed in claim 16, wherein the coding sequence comprising a nucleotide sequence selected from the group consisting of: the nucleotide sequence as set forth in SEQ ID NOs: 4-6 is root-specific expression.

24. A method for inducing a gene expression, comprising:
   a step of providing a plant, plant part or plant cell containing the recombinant nucleic acid molecule according to claim 2, and
   a step of treating the plant, plant part or plant cell by a stress treatment,
   wherein the stress treatment comprises a jasmonic acid, jasmonate, sodium chloride, abscisic acid, dehydration or mechanical stress.

25. The method as claimed in claim 24, wherein the expression of the coding sequence comprises a stable or transient expression.

26. The method as claimed in claim 24, wherein the plant part comprises a root, stem, leaf, flower or silique.

27. The method as claimed in claim 24, wherein the plant is selected from the group consisting of a tomato, tobacco, kenaf or *Arabidopsis*.

28. The method as claimed in claim 24, wherein the expression of the coding sequence operably linked to the promoter comprising a nucleotide sequence selected from the group consisting of: the nucleotide sequence as set forth in SEQ ID NOs: 4-6 is root-specific.

* * * * *